(12) United States Patent
Margolin

(10) Patent No.: US 6,956,044 B1
(45) Date of Patent: Oct. 18, 2005

(54) COMPOSITIONS AND METHODS FOR TREATMENT OF EPILEPSY

(76) Inventor: Solomon B. Margolin, 6723 Desco Dr., Dallas, TX (US) 75225

( * ) Notice: Subject to any disclaimer, the term of this patent is extended or adjusted under 35 U.S.C. 154(b) by 0 days.

(21) Appl. No.: 10/204,605

(22) PCT Filed: Feb. 21, 2000

(86) PCT No.: PCT/US00/05221

§ 371 (c)(1),
(2), (4) Date: Dec. 10, 2002

(87) PCT Pub. No.: WO01/62253

PCT Pub. Date: Aug. 30, 2001

(51) Int. Cl.[7] .............................................. A01N 43/40

(52) U.S. Cl. ...................................... 514/315; 514/327
(58) Field of Search .................................. 514/315, 327

(56) References Cited

U.S. PATENT DOCUMENTS

| | | | | |
|---|---|---|---|---|
| 2,947,755 A | * | 8/1960 | Scudi et al. ................. | 260/296 |
| 5,962,478 A | * | 10/1999 | Margolin ..................... | 514/345 |
| 6,090,822 A | * | 7/2000 | Margolin ..................... | 514/313 |

* cited by examiner

*Primary Examiner*—Kevin E. Weddington
(74) *Attorney, Agent, or Firm*—John H. Crozier

(57) ABSTRACT

A method of treating a mammal with an epileptic condition, comprising: administering to said mammal a pharmaceutical composition containing an effective amount of an N-phenyl substituted 2-pyridone compound and/or pharmaceutically acceptable salts thereof.

1 Claim, No Drawings

COMPOSITIONS AND METHODS FOR TREATMENT OF EPILEPSY

CROSS-REFERENCE TO RELATED APPLICATION

The present application is a filing under 35 USC 371 of Patent Cooperation Treaty Patent Application Serial No. PCT/US00/05221, filed Feb. 21, 2000, and titled COMPOSITIONS AND METHODS FOR TREATMENT OF EPILEPSY.

TECHNICAL FIELD

This invention relates to certain synthesized organic compounds which demonstrate pharmacological actions characteristic of anticonvulsant (anti-epileptic) properties. The invention is based upon the discovery and demonstration that certain N-phenyl substituted 2-pyridones have marked sustained anti-convulsant properties, and suitably low levels of untoward effects.

BACKGROUND ART

Epilepsies are a group of disorders characterized by chronic and paroxysmal alterations in neurologic function associated with deviate changes in the electrical activity of the brain. They are estimated to occur between 0.5% and 2.0 percent of the population, and may occur at any age ("Harrison's Principles of Internal Medicine," 13th Edition, 1994, Isselbacher et al., Editors, McGraw-Hill, New York). Each episode of this type neurologic dysfunction is called a seizure. They may be convulsive when accompanied by motor manifestations, or may be manifest by other abnormal changes in neurologic function such as sensory, cognitive, or emotional events. Epilepsy can be induced as a result of neurologic injury or a structural brain lesion that can occur as part of other known systemic medical disorders.

About 3.0% of the United States population has recurrent, unprovoked epilepsy (W. A. Hauser, and D. C. Hesdorfer, "Epilepsy: Frequency, Causes and Consequences," New York: Demos., 1990, 21–28). The estimated prevalence of active epilepsy is 6.4 cases per 1000 population. This means that over 1.5 million people have active epilepsy manifest as seizures (A. V. Delgado-Escueta et al., *Adv. Neurol.*, 44: 1–120, 1986).

The annual incidence of epilepsy ranges from 20 to 70 cases per 100,000 (S. D. Shorvon, *Lancet*, 1990, 336: 93–96). About 30% of patients with seizures have an identifiable neurologic or systemic disorder (D. W. Chadwick, *Lancet*, 1990, 336: 291–295), and the remainder have idiopathic or cryptogenic epilepsy. The diagnosis is based on the description of the seizures and the clinical context in which they occur. This is often further supplemented by results obtained EEG evaluations. Epileptic seizures have varied manifestations, and it becomes important to endeavor to classify the kind of seizure in order to select an appropriate and effective treatment. Since it is important to classify the type of seizure to choose the most suitable medical treatment, a useful classification of seizures, based on that structured by the International League against Epilepsy in 1981 is outlined in Table 1:

TABLE 1

CLASSIFICATION OF EPILEPTIC SEIZURES**

Primary Generalized Seizures (convulsive or non-convulsive)

Tonic-Clonic (grand mal)
Tonic
Absence (petit mal)
Atypical absence
Myoclonic
Atonic
Infantile spasms
Partial or Focal Seizures (beginning locally)

Simple partial seizures (without impaired consciousness)

With motor symptoms
With somatosensory or special sensory symptoms
With autonomic symptoms
With psychological symptoms
Complex partial seizures (with impaired consciousness)

Simple partial onset followed by impaired consciousness
Impaired consciousness at onset

**"Harrison's Principles of Internal Medicine," 13th Edition, 1994, Isselbacher et al., Editors, McGraw-Hill, New York; M. J. Brodie and M. A. Dichter, N. E. Jour. Med., 334:168–175, 1996.

The pathologic origins of many seizure foci in the human brain include congenital defects, head trauma and hypoxia at birth, inflammatory vascular changes subsequent to infectious pediatric illnesses, concussions or depressed skull fracture, abscess, neoplasm, vascular occlusion.

Epilepsy is a complex disease process with various, little-understood etiologies. Despite the variety of drugs used in humans to treat epileptic seizures, 20 to 40% of epileptic patients fail to experience satisfactory seizure control with currently available drugs. A clinically useful anticonvulsant drug can affect either the initiation of an epileptic discharge, or its spread within the brain. In either case, the drug ultimately must attenuate or alter neuronal excitability. This may be attained by at least three different mechanisms: modulation of voltage-dependent ions channels, enhancement of inhibitory pathways in the CNS, or suppression of excitatory pathways (Rogawski et al., 1990, *Pharmacol. Rev.*, 42: 223–286).

Two general ways are currently thought to characterize the ways by which drugs might attenuate or abolish seizures: (1) effects on pathologically altered neurons at seizure foci to prevent or reduce their initiating excessive discharge, and (2) effects that may impede or block the spread of the excitation from the initiating foci, and thereby prevent detonation and the associated disruption of normal function by aggregates of neurons located quite distant from the seizure foci. As to our knowledge of the mechanisms of action at the intracellular or molecular level, it must be admitted that mechanisms for the beneficial action of anti-epileptic agents remains poorly understood, but is currently an expanding region for many neurological investigations.

The physician who treats patients with epilepsy encounters the task of selecting an appropriate drug or combination of drugs that may best control, seizures in a given patient at an acceptable level of adverse effects. Generally, complete control (90–100%) of seizures may be attained in as much as 50% of patients, and another 25% may evidence significant reductions in the incidence of seizures.

The classification of seizures given in the above table may be further simplified in terms of clinical experience. Absence seizures respond well to one group of drugs, and generalized tonic-clonic convulsions are generally well controlled by another. Complex partial seizures tend to be refractory to any therapy, but may show some response to the second group.

Infantile spasm and akinetic, atonic and myoclonic seizures are groups which respond very inadequately to the above two classes of drugs. Furthermore, more than one anticonvulsant drug may be required to treat patients diagnosed with two or more types of seizures (L. Goodman and A. Gilman, "The Pharmacoloical Basis of Therapeutics," 7th Ed., 1985, MacMillan, New York; 8th Ed., 1990, Mac-Millan-Pergamon, New York).

Experimentally Induced Seizures. The electroshock technique for producing experimental convulsions in the intact animal for testing chemical substances for anticonvulsant activity (T. J. Putnam and H. H. Merritt, 1937, *Science*, 85: 525–526) provided a practical means for the evaluation of chemical agents for the management of epilepsy prior to their administration to man. Their demonstration of anticonvulsant action and anti-epileptic efficacy of phenytoin was provided a successful treatment for many patients with uncontrolled epilepsy. The success of their animal testing program showed that an experimental method could lead to the discovery of compounds that would be clinically effective. R. K. Richards and G. M. Everett, 1944 (*Fed. Proc.*, 3: 39) found that trimethadione prevented threshold seizures induced in rodents with pentylenetetrazol, and that such seizures were also prevented by phenobarbital, but not by phenytoin. Subsequently, Goodman and associates (*Proc. Am. Fed. Clin. Res.*, 2: 100–101, 1945; *Jour. Phamacol. Exper. Ther.*, 108: 168–176, 1953) found that that phenytoin and phenobarbital, but not trimethadione, modified that pattern of experimental maximal electroshock seizures. These cited researches demonstrated in animals the significant different clinical anticonvulsant actions of these drugs. W. G. Lennox (*Jour. Am. Med. Assn.*, 129: 1069–1074, 1945; *Jour. Am. Med. Assn.*, 134: 138–143, 1947) found that trimethadione was effective in epileptic patients suffering from petit mal, as well as myoclonic or akinetic seizures that could not be controlled by phenytoin or phenobarbital. He also found that trimethadione decreased or stopped their petit mal attacks, but failed to control grand mal attacks in 10 patients in which this type of seizure predominated (R. L. Krall et al., *Epilepsia*, 19: 193–408, 1978).

DISCLOSURE OF INVENTION

The present invention achieves the above objects, among others, by providing, in a preferred embodiment, a method of treating a mammal with an epileptic condition, comprising: administering to said mammal a pharmaceutical composition containing an effective amount of an N-phenyl substituted 2-pyridone compound and/or pharmaceutically acceptable salts thereof.

BEST MODE FOR CARRYING OUT THE INVENTION

The present invention relates to the novel use of N-phenyl substituted 2-pyridone compounds having the general formula:

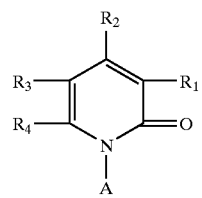

where:
R1 is selected from the group consisting of (1) an alkyl group, with R3 hydrogen, and (2) hydrogen, with R3 consisting of an alkyl group; A is an aryl group/and R2 and R4 are hydrogen.

These compounds, including pirfenidone, 5-methyl-1-phenyl-2(1H)pyridone, possess remarkable anti-convulsant properties in widely accepted experimental models of epileptic seizures. The preclinical pharmacologic and neuropharmacologic experimental tests suggest (1) oral and parenteral efficacy quite suitable for treating, various types of human epilepsy seizures and (2) a low level of side effects reflecting an absence of serious adverse reactions (absence of gum hyperplasia, absence of depressed bone marrow function, absence of liver or kidney damage). The safety profile for humans suggested in laboratory animal toxicity experiments appears is consistent with the low incidence of any serious adverse reactions seen thus far in more than 300 human patients with other, non-epileptic disorders (J. E. Walker *ACTRIMS*, (Montreal, Canada), Oct. 18, 1998; G. Rahgu et al., *Amer. Respir. Crit. Care Med.*, 159: 1061–1069, 1999; M. Taniyama et al., *Eur. Jour. Clin. Pharmacol.*, 52: 77–78, 1997), and unpublished inventor's human patient files.

In laboratory animals or in man, pirfenidone is well absorbed after oral administration. Plasma pirfenidone concentrations in man peak 1 to 4 hours after dosing. Metabolically, first order kinetics prevail over a daily dose range of 1200 to 3600 milligrams of pirfenidone in divided dosage (t.i.d.). Pirfenidone is cleared primarily by hepatic metabolism (S. Giri et al., *Amer. Thoracic Soc. International Conf.*, Apr. 24–29, 1998) mainly hydroxylation and conjugation, and excreted primarily in the urine. None of its metabolites appears to be active against rodent experimental seizures.

The mechanism of action of pirfenidone in experimental seizures as gauged from neuropharmaclogical tests in cat and frog demonstrations, and (see below) is very similar to that of phenytoin to the extent that pirfenidone, like phenytoin, can completely block the classical after-discharge when a nerve is electronically stimulated. However, the molecular mechanism of the anticonvulsant action within neuronal cells remains unknown.

Pirfenidone has a low level of sedative properties as compared to the effective dose levels in laboratory experiments, and its low level of sedative activity has been observed in various human clinical trials.

The compounds can be given orally in various dosages forms, such as tablets, capsules, or solutions, or by parenteral injection in the form of suitable sterile solutions.

For humans, the effective anticonvulsant oral daily dosages of the present compounds range between 5.0 and 40.0 mg/kg body weight in divided dosages (q.i.d. or t.i.d.), and the parenteral dosages range between 2.0 and 20.0 mg/kg body weight (q.i.d. or t.i.d.). Special oral pharmceutically based long-acting formulations can be prepared to reduce dosing to only once or twice daily.

Representative 2-pyridones and reference compounds compared are:
5-methyl-1-phenyl-2(1H)-pyridone (pirfenidone)
3-methyl-1-phenyl-2(1H)-pyridone
5-ethyl-1-phenyl-2(1H)-pyridone
1-phenyl-2(1H)-pyridone
phenytoin (Dilantin)

Effect Against Maximal Electroshock Seizures. In laboratory experimental studies by this technique, two effective compounds (5-methyl or 5-ethyl substituted, 1-phenyl 2-pyridones) possess anti-convulsant properties that approach that known for phenytoin, a standard anticonvulsant drug for grand mal seizures. Given intraperitoneally to albino mice these compounds have afforded complete protection from maximal electroshock seizures for several hours.

To test the maximal seizure anticonvulsant properties in albino mice weighing approximately 25 grams, first an electrical current was delivered via cranial electrodes at a voltage strength which induced a typical maximal electroconvulsant seizure in all the mice. Maximal tonic electrochock seizures were induced with 2 to 7 milliamperes being discharged at 18 volts, and at a frequency of 1000 per second. Abolition of the hindlimb tonic extension component of the seizure was defined as protection in this maximal electroshock test (L. S. Goodman et al., *Jour. Pharm. Exper. Therap.*, 108: 168, 1953). The apparatus used was structured so that the current administered was independent of external resistance. There were 10 animals per group, and they were exposed to electroshock seizures at 20, 80 and 140 minutes after injection of the test compounds. The mice received graded doses of the compounds, and the dose protecting 50% of the animals was calculated biometrically. Table 2 displays the calculated respective intraperitoneal doses protecting 50 percent of the mice against maximal electroshock seizures.

These results demonstrate that two (5-methyl and 5-ethyl) substituted N-phenyl-2-pyridones are superior to the other 2-pyridones tested. The protection lasted for about 3 hours, despite the fact that the two most effective compounds are known to be very rapidly metabolized in mice or rats (as compared to dogs or humans).

Oral or parenteral pirfenidone is readily and uniformly absorbed from the gastrointestinal tract or injection site, respectively, of laboratory animals. Oral pirfenidone is readily and uniformly absorbed from the gastrointestinal tract. Although the studied 2-pyridones are rapidly metabolized in small rodents, in rabbits, dogs, and in human subjects pirfenidone is clearly slowly metabolized as demonstrated after single dose and repeat dosage studies (S. B. Margolin and S. Lefkowitz, *FASEB Jour.*, 8: A382, 1994; M. Taniyama et al., *Eur. Jour. Clin. Pharmacol.*, 52: 77–78, 1997; S. Giri et al., *Amer. Thoracic Soc. Intern. Conf.*, Apr. 24–29, 1998).

TABLE 2

| | I.P. ED50** MG/KG | I.P. LD50 MG/KG |
|---|---|---|
| 5-methyl-1-phenyl-2-(1H)-pyridone (pirfenidone) | 85 +/− 11 | 600 +/− 43 |
| 3-methyl-1-phenyl-2-(1H)-pyridone | No Activity | >500 |
| 5-ethyl-1-phenyl-2-(1H)-pyridone | 60 +/− 10 | 500 +/− 61 |
| 1-phenyl-2-(1H)-pyridone | No Activity | >500 |
| phenytoin (Dilantin) | 50 +/− 15 | 200 +/− 45 |

**140 minutes after injection of test compound.

The highly rapid and efficient oral bioavailability of pirfenidone in humans contrasts with that of oral phenytoin. In man, absorption of phenytoin after oral ingestion is slow, often variable and can be incomplete so that peak or effective concentrations in plasma and tissues may be delayed for 3 or more hours (E. Perucca and A. Richens, "Handbook of Exper. Pharmacol.," Vol. 74: 831–855, 1985, Springer-Verlag, Berlin.)

Effect Against Pentylenetetrazol (Metrazol) Seizures. Table 2 displays the calculated respective oral doses protecting 50% of the mice against pentylenetetrazol-induced seizures. The pentylenetetrazol (metrazol), 120 mg/kg, was injected intraperitoneally 30 minutes after the oral administration of the respective graded doses of the compounds. Protection in this test was defined as a failure to detect even a single episode of clonic spasms of at least 5 seconds duration during a 30 minute period following the injection of the metrazol (F. M. Berger, 78:277, 1951). Phenytoin is known to be inactive *Proc. Soc. Exper. Med. Biol.*, against pentylenetetrazol seizures (R. L. Krall et al., *Epilepsia*, 19: 193–408, 1978).

Among the cited 2-pyridones, the 5-methyl or 5-ethyl substituted compounds possess distinct neuropharmacologic effects characteristic of a standard anticonvulsant such as phenytoin.

TABLE 3

| | ORAL ED50 MG/KG | ORAL LD50 MG/KG |
|---|---|---|
| 5-methyl-1-phenyl-2-(1H)-pyridone (pirfenidone) | 325 +/− 41 | 610 +/− 34 |
| 3-methyl-1-phenyl-2-(1H)-pyridone | No Activity | 650 +/− 110 |
| 5-ethyl-1-phenyl-2-(1H)-pyridone | 285 +/− 29 | 425 +/− 48 |
| 1-phenyl-2-(1H)-pyridone | No Activity | 540 +/− 124 |
| phenytoin (Dilantin) | No Activity | 490 +/− 35 |

Pirfenidone: Effect on Frog Sciatic Nerve Trunk High Frequency Stimulation. Bullfrog sciatic nerve trunk (desheathed) was stimulated with trains of pulses at 200 Hertz in order to see if pirfenidone affected the nerve's ability to conduct high frequency impulses. At a high concentration of 10 mM, the drug caused definite high frequency failure, although it did not cause local anesthesia in the nerve. Drugs that cause "use-dependent" block (high frequency failure) are generally regarded as potential anti-epileptic drugs.

Pirfenidone: Effect on Neuromuscular Function of the Cat Soleus Muscle Nerve Preparation. In experiments with the cat soleus muscle nerve preparation (Raines and Standaert, *Epilepsia*, 10: 211, 1969), pirfenidone, 50 mg/kg intravenously, suppresses the post-tetanic potentiation (PTP). The action resembles that of phenytoin (J. A. Wada, *Arch. Neurol.*, 34: 389–395, 1977). Neither pirfenidone nor phenytoin impair single impulse transmission. Since the PTP effect, as seen in the soleus muscle, arises from a stimulus-initiated burst of nerve firing, its suppression is equivalent to an anti-epileptic (anticonvulsant) action.

Examples of 2-pyridones found to be, or believed to be, effective in treating epilepsy are:
5-Methy-1-phenyl-2(1H)-pyridone
5-Methyl-1-(3-nitrophenyl)-2-(1H)-pyridone
5-Methyl-1-(4'-methoxyphenyl)-2-(1H)-pyridone
5-Methyl-1-p-tolyl-2-(1H)-pyridone
5-Methyl-1-(3'-trifluoromethylphenyl)-2-(1H)-pyridone
1-(4'-Chlorophenyl)-5-methyl-2-(1H)-pyridone
5-Methyl-1-(2'-naphthyl)-2-(1H)-pyridone
5-Methyl-1-(1'-naphthyl)-2-(1H)-pyridone
3-Ethyl-1-phenyl-2-(1H)-pyridone
6-Methyl-1-phenyl-2-(1H)-pyridone 3,6-Dimethyl-1-phenyl-2-(1H)-pyridone
5-Methyl-1-(2'-thienyl)-2-(1H)-pyridone
1-(2'-Furyl)-5-methyl-2-(1H)-pyridone
5-Methyl-1-(5'-quinolyl)-2-(1H)-pyridone
5-Methyl-1-(4'-pyridyl)-2-(1H)-pyridone
5-Methyl-1-(3'-pyridyl)-2-(1H)-pyridone
5-Methyl-1-(2'-pyridyl)-2-(1H)-pyridone
5-Methyl-1-(2'-quinolyl)-2-(1H)-pyridone
5-Methyl-1-(4'-quinolyl)-2-(1H)-pyridone
5-Methyl-1-(2'-thiazolyl)-2-(1H)-pyridone
1-(2'-Imidazolyl)-5-methyl-2-(1H)-pyridone
5-Ethyl-1-phenyl-2-(1H)-pyridone
1-(4'-Nitrophenyl)-2-(1H)-pyridone
1,3-Diphenyl-2-(1H)-pyridone
1-Phenyl-3-(4'-chlorophenyl)-2-(1H)-pyridone
1,3-Diphenyl-5-methyl-2-(1H)-pyridone
3-(4'-Chlorophenyl)-5-methyl-1-phenyl-2-(1H)-pyridone
5-Methyl-3-phenyl-1-(2'-thienyl)-2-(1H)-pyridone It will thus be seen that the objects set forth above, among those elucidated in, or made apparent from, the preceding description, are efficiently attained and, since certain changes may be made in the above invention without departing from the scope of the invention, it is intended that all matter contained in the above description shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A method of treating a mammal with an epileptic condition, comprising: administering to said mammal a pharmaceutical composition containing an effective amount of an N-phenyl substituted 2-pyridone compound and/or pharmaceutically acceptable salts thereof, said N-phenyl compound comprising one or more compounds selected from the group consisting of:

5-Methy-1-phenyl-2(1H)-pyridone; and
5-Ethyl-1-phenyl-2-(1H)-pyridone.

* * * * *

UNITED STATES PATENT AND TRADEMARK OFFICE
CERTIFICATE OF CORRECTION

| | |
|---|---|
| PATENT NO. | : 6,956,044 B1 |
| DATED | : October 18, 2005 |
| INVENTOR(S) | : Solomon B. Margolin |

It is certified that error appears in the above-identified patent and that said Letters Patent is hereby corrected as shown below:

Column 6,
Line 8, should read -- Table 3 --.

Signed and Sealed this

Seventh Day of March, 2006

JON W. DUDAS
*Director of the United States Patent and Trademark Office*